US00PP17962P2

(12) United States Plant Patent
Schräder

(10) Patent No.: US PP17,962 P2
(45) Date of Patent: Aug. 28, 2007

(54) ***THUNBERGIA* PLANT NAMED 'SUMTHUN 02'**

(50) Latin Name: *Thunbergia alata*
Varietal Denomination: Sumthun 02

(76) Inventor: Ralf Schräder, Karl-Leisner-Str. 15, 59348 Lüdinghausen (DE)

( * ) Notice: Subject to any disclaimer, the term of this patent is extended or adjusted under 35 U.S.C. 154(b) by 0 days.

(21) Appl. No.: 11/358,920

(22) Filed: Feb. 17, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Thunbergia* plant named 'Sumthun 02', characterized by its upright, climbing and vigorous growth habit; freely branching habit; dense and bushy appearance; freely flowering habit; and large orange-colored flowers with a purple-colored throat.

2 Drawing Sheets

Botanical designation: *Thunbergia alata.*
Cultivar denomination: 'Sumthun 02'.

BACKGROUND OF THE INVENTION

The present Invention relates to a new and distinct cultivar of *Thunbergia* plant, botanically known as *Thunbergia alata,* and hereinafter referred to by the cultivar name 'Sumthun 02'.

The new *Thunbergia* is a product of a planned breeding program conducted by the Inventor in Lüdinghausen, Germany. The objective of the breeding program is to develop new *Thunbergia* cultivars with large flowers and unique and attractive flower coloration.

The new *Thunbergia* originated from a cross-pollination made by the Inventor in April, 2003 of a proprietary selection of *Thunbergia* identified as code number 2-18, not patented, as the female, or seed, parent with a proprietary selection of *Thunbergia* identified as code number 2-3, not patented, as the male, or pollen, parent. The new *Thunbergia* was discovered and selected by the Inventor in a controlled environment in Lüdinghausen, Germany as a single plant within the resulting progeny from the stated cross-pollination in August, 2003.

Asexual reproduction of the new cultivar by terminal cuttings at Lüdinghausen, Germany since September, 2003, has shown that the unique features of this new *Thunbergia* are stable and reproduced true to type in successive generations.

SUMMARY OF THE INVENTION

Plants of the cultivar Sumthun 02 have not been observed under all possible environmental conditions. The phenotype may vary with variations in environment such as temperature and light intensity without, however, any variance in genotype.

The following traits have been repeatedly observed and are determined to be the unique characteristics of 'Sumthun 02'. These characteristics in combination distinguish 'Sumthun 02' as a new and distinct cultivar of *Thunbergia:*

1. Upright, climbing and vigorous growth habit.
2. Freely branching habit; dense and bushy appearance.
3. Freely flowering habit.
4. Large orange-colored flowers with a purple-colored throat.

Plants of the cultivar Sumthun 02 can be compared to plants of the female parent selection. In side-by-side comparisons conducted in Lüdinghausen, Germany, plants of the new *Thunbergia* differed from plants of the female parent selection in the following characteristics:

1. Plants of the new *Thunbergia* were larger than plants of the female parent selection.
2. Plants of the new *Thunbergia* had larger flowers than plants of the female parent selection.

Plants of the cultivar Sumthun 02 can be compared to plants of the male parent selection. In side-by-side comparisons conducted in Lüdinghausen, Germany, plants of the new *Thunbergia* differed primarily from plants of the male parent selection in flower color.

Plants of the new *Thunbergia* can also be compared to plants of the *Thunbergia* cultivar Orange Eye, not patented. In side-by-side comparisons conducted in Lüdinghausen, Germany, plants of the new *Thunbergia* differed from plants of the cultivar Orange Eye in the following characteristics:

1. Plants of the new *Thunbergia* were larger than plants of the cultivar Orange Eye.
2. Plants of the new *Thunbergia* had thicker stems than plants of the cultivar Orange Eye.
3. Plants of the new *Thunbergia* were more freely flowering than plants of the cultivar Orange Eye.
4. Plants of the new *Thunbergia* had larger flowers than plants of the cultivar Orange Eye.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Thunbergia*.

The photograph on the first sheet comprises a side perspective view of a typical flowering plant of 'Sumthun 02' grown in a container.

The photograph on the second sheet is a close-up view of typical flowers of 'Sumthun 02'.

DETAILED BOTANICAL DESCRIPTION

Plants used in the aforementioned photographs and for the following description were grown under conditions which closely approximate commercial production conditions during the spring and summer in an outdoor nursery in L üdinghausen, Germany. Plants were about four months old. During the production of the plants, the day temperatures ranged from 16° C. to 30° C., night temperatures ranged from 8° C. to 14° C. and light levels ranged from 45,000 to 70,000 lux. In the following description, color references are made to The Royal Horticultural Society Colour Chart, 2001 Edition, except where general terms of ordinary dictionary significance are used.

Botanical classification: *Thunbergia alata* cultivar Sumthun 02.

Parentage:

*Female parent.*—Proprietary selection of *Thunbergia alata* identified as 2-18, not patented.

*Male parent.*—Proprietary selection of *Thunbergia alata* identified as 2-3, not patented.

Propagation:

*Type cutting.*—Terminal vegetative cuttings.

*Time to initiate roots, summer.*—About three weeks at 16° C.

*Time to initiate roots, winter.*—About four weeks at 16° C.

*Time to produce a rooted young plant.*—About five weeks at 16° C.

*Root description.*—Fine, fibrous; color, 162C.

*Rooting habit.*—Freely branching; moderately dense.

Plant description:

*Form.*—Annual flowering plant; upright to climbing plant habit; uniformly mounded. Freely branching with lateral branches potentially forming at every node. Vigorous growth habit.

*Usage.*—Appropriate for hanging baskets, window boxes and patio containers.

*Plant height (from soil level to top of plant plane).*—About 250 cm to 350 cm.

*Plant length (from soil level to lateral branches apices).*—About 150 cm.

*Lateral branch description.*—Length: About 200 cm. Diameter: About 3 mm to 5 mm. Internode length: About 1 cm to 1.2 cm. Texture: Pubescent. Color: 200B.

*Foliage description.*—Arrangement: Opposite, simple. Length: About 5 cm to 6 cm. Width: About 4.5 cm to 5 cm. Shape: Lanceolate. Apex: Acuminate. Base: Cordate. Margin: Slightly serrate. Texture, upper and lower surfaces: Pubescent. Venation: Pinnate. Color: Developing foliage, upper surface: 143B to 143C. Developing foliage, lower surface: 146D. Fully expanded foliage, upper surface: 137A to 137B; venation, 146A to 146B. Fully expanded foliage, lower surface: 138A to 138B; venation, 146A to 146B. Petiole length: About 2 cm to 2.5 cm. Petiole diameter: About 1 mm. Petiole texture, upper and lower surfaces: Smooth. Petiole color, upper and lower surfaces: 146C.

Flower description:

*Flower type and habit.*—Large salverform flowers; flowers face mostly outwardly; flowers single, axillary. Flowers not persistent. Freely flowering habit with about 13 to 20 flower buds and open flowers per lateral branch. Flowers not fragrant.

*Natural flowering season.*—Early spring until frost in the autumn; flowering continuous during this period.

*Flower longevity on the plant.*—About five days.

*Flower buds.*—Length: About 2.5 cm. Diameter: About 2 mm. Shape: Oblong. Color: 143C to 143D.

*Flower size.*—Diameter: About 4.5 cm to 5 cm. Depth (height): About 2.5 cm.

*Corolla.*—Arrangement/appearance: Single whorl of five petals, fused into flared trumpet. Petal length from throat: About 2 cm. Petal width: About 2.2 cm. Petal shape: Roughly spatulate with a shallow cordate apex. Petal margin: Entire. Petal texture, upper and lower surfaces: Smooth, glabrous; satiny. Color: Petal, when opening, upper surface: 25A; towards the center, overlain with 187A. Petal, when opening, lower surface: 25C to 25D. Petal, fully opened, upper surface: 25A; towards the center, overlain with 187A; color becoming closer to 28A with development. Petal, fully opened, lower surface: 25D. Flower throat (inside): 187A. Flower tube (outside): 25C to 25D.

*Sepals.*—Arrangement/appearance: Single whorl of about nine sepals, star-shaped. Length: About 1.5 cm to 2 cm. Width: About 0.5 mm. Shape: Lanceolate. Apex: Acute. Base: Truncate. Margin: Entire. Texture, upper and lower surfaces: Smooth. Color, upper and lower surfaces: 145D.

*Peduncles.*—Length: About 10 cm to 12 cm. Width: About 1 mm. Strength: Strong. Texture: Pubescent. Color: 144B.

*Reproductive organs.*—Stamens: Quantity per flower: Four to five. Anther shape: Oblong. Anther length: About 3 mm. Anther color: 11D. Pollen amount: Moderate. Pollen color: 11D. Pistils: Quantity per flower: One. Pistil length: About 7 mm. Stigma shape: Bi-parted. Stigma color: 145D. Style length: About 1 mm. Style color: 145D. Ovary color: Close to 145A. Seeds: Length: About 3 mm. Diameter: About 2 mm. Color: 200A.

Disease/pest resistance: Plants of the new *Thunbergia* have not been noted to be resistant to pathogens and pests common to *Thunbergia*.

Temperature tolerance: Plants of the new *Thunbergia* have been observed to tolerate temperatures ranging from about 1° C. to about 35° C.

It is claimed:

1. A new and distinct cultivar of *Thunbergia* plant named 'Sumthun 02', as illustrated and described.

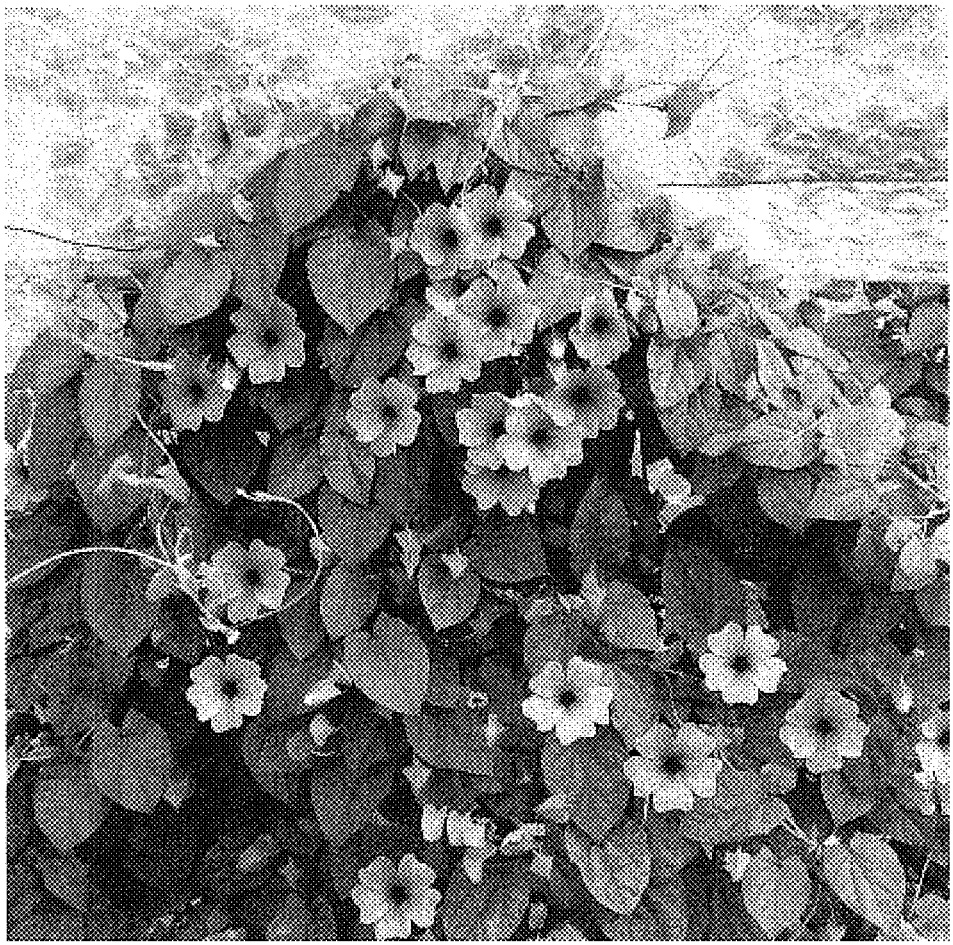

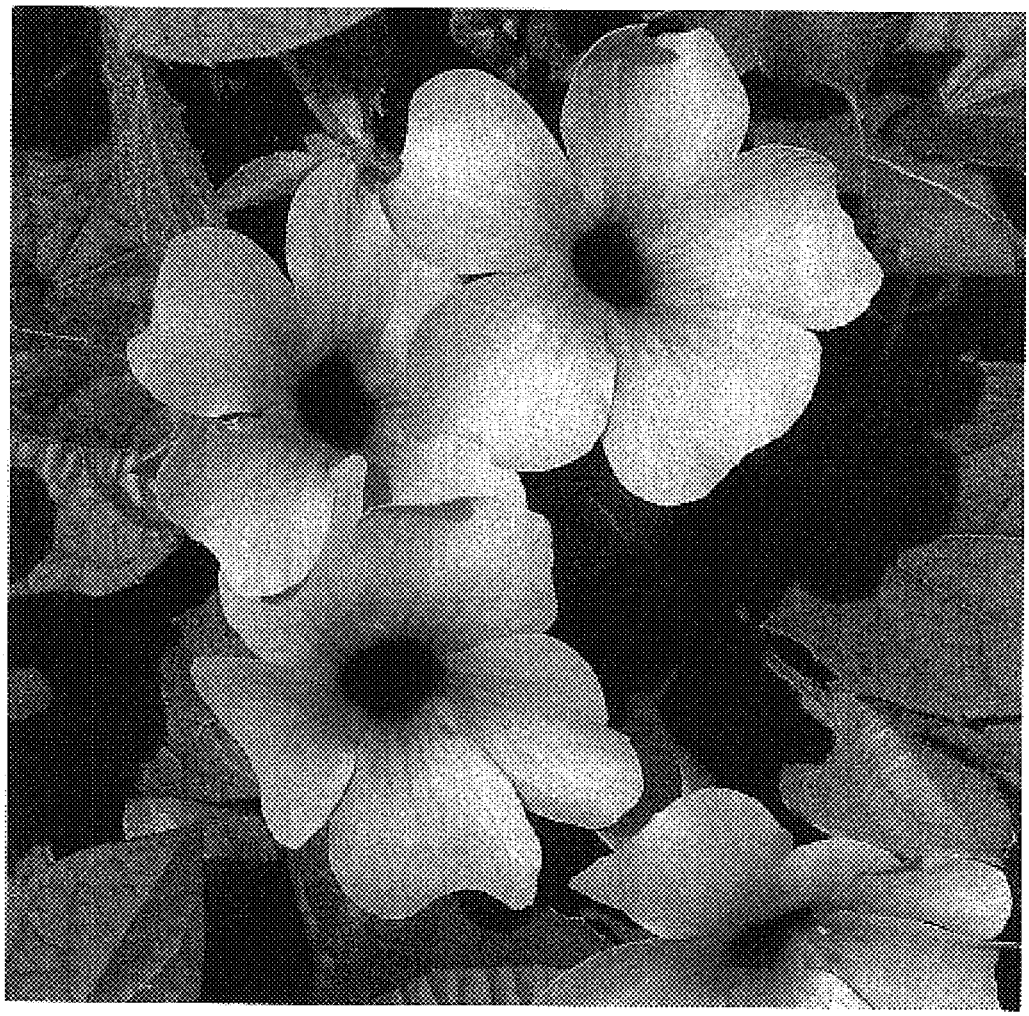

* * * * *